(12) United States Patent
Bossler (10) Patent No.: US 9,526,589 B2
(45) Date of Patent: Dec. 27, 2016

(54) CONCENTRICITY-OPTIMIZED TOOL CLAMPING SYSTEM FOR DENTAL ANGLED HANDPIECES AND DENTAL TURBINES

(71) Applicant: Minebea Co., Ltd., Nagano-ken (JP)

(72) Inventor: Juergen Bossler, Leutkirch (DE)

(73) Assignee: MINEBEA CO., LTD., Nagano-Ken (JP)

( * ) Notice: Subject to any disclaimer, the term of this patent is extended or adjusted under 35 U.S.C. 154(b) by 356 days.

(21) Appl. No.: 14/089,964

(22) Filed: Nov. 26, 2013

(65) Prior Publication Data

US 2014/0154642 A1    Jun. 5, 2014

(30) Foreign Application Priority Data

Nov. 30, 2012 (DE) .................. 10 2012 023 437

(51) Int. Cl.
*A61C 1/14* (2006.01)
*B23B 31/20* (2006.01)

(52) U.S. Cl.
CPC ............ *A61C 1/144* (2013.01); *A61C 1/141* (2013.01); *B23B 31/207* (2013.01); *B23B 2231/2078* (2013.01); *Y10T 279/17307* (2015.01); *Y10T 279/17341* (2015.01)

(58) Field of Classification Search
CPC ............ B23B 31/207; B23B 2231/2078; A61C 1/141; A61C 1/144; Y10T 279/17307; Y10T 279/17341; Y10T 279/17521
See application file for complete search history.

(56) References Cited

U.S. PATENT DOCUMENTS

| 2,176,071 | A | * | 10/1939 | Hall | ............... | B23B 31/207 |
| | | | | | | 279/53 |
| 4,874,314 | A | * | 10/1989 | Fleer | ............... | A61C 1/141 |
| | | | | | | 279/43 |
| 5,165,896 | A | * | 11/1992 | Hain | ............... | A61C 1/141 |
| | | | | | | 433/127 |
| 5,571,013 | A | * | 11/1996 | Novak | ............... | A61C 1/181 |
| | | | | | | 433/127 |
| 5,688,122 | A | * | 11/1997 | Teufelberger | ............... | A61C 1/141 |
| | | | | | | 433/127 |
| 5,833,704 | A | | 11/1998 | McCombs et al. | | |
| 5,836,766 | A | * | 11/1998 | Gugel | ............... | A61C 1/144 |
| | | | | | | 415/904 |
| 5,911,578 | A | * | 6/1999 | Gross | ............... | A61C 1/144 |
| | | | | | | 279/125 |
| 6,155,826 | A | * | 12/2000 | Howard | ............... | A61C 1/144 |
| | | | | | | 433/129 |
| 6,190,168 | B1 | * | 2/2001 | Bowen | ............... | A61C 1/144 |
| | | | | | | 433/127 |
| 7,074,041 | B2 | * | 7/2006 | Kuhn | ............... | A61C 1/141 |
| | | | | | | 433/127 |
| 7,815,433 | B2 | * | 10/2010 | Bailey | ............... | A61B 17/162 |
| | | | | | | 433/129 |

(Continued)

FOREIGN PATENT DOCUMENTS

DE    102010037791    3/2012

*Primary Examiner* — Eric A Gates
(74) *Attorney, Agent, or Firm* — Cooper & Dunham LLP (57) ABSTRACT

A clamping device for a dental tool in a dental turbine handpiece having at least one clamping lever. The clamping lever permits a tool shank to be clamped.
The structure allows for more accurate relative positioning and improved concentricity of the dental tool after clamping.

6 Claims, 5 Drawing Sheets

(56) References Cited

U.S. PATENT DOCUMENTS

| | | | |
|---|---|---|---|
| 2002/0105149 A1 | 8/2002 | Karst | |
| 2007/0031786 A1* | 2/2007 | Heil | A61C 1/08 433/129 |
| 2007/0087308 A1* | 4/2007 | Flock | A61C 1/141 433/132 |
| 2007/0243499 A1 | 10/2007 | Bowen | |
| 2009/0142730 A1* | 6/2009 | Pernot | A61C 1/144 433/128 |
| 2012/0244495 A1* | 9/2012 | Bossler | A61C 1/141 433/127 |

\* cited by examiner

CONCENTRICITY-OPTIMIZED TOOL CLAMPING SYSTEM FOR DENTAL ANGLED HANDPIECES AND DENTAL TURBINES

The invention relates to a clamping device for clamping a dental tool in a dental turbine handpiece, used particularly for high-speed air turbines that operate at high rotational speeds of about 200,000 to 500,000 rpm.

PRIOR ART

The basic requirement placed on a clamping device for a dental tool in a dental turbine handpiece is that the dental tool can be exchanged using the least possible operating force and without the need for additional tools. However, at the same time the operating force must not be made too weak, since there would then be the risk of inadvertent operation. The holding force must be strong enough to clamp the dental tool firmly and securely under all operating conditions. It is thus desirable to have a clamping system that is quickly and easily operated and that has sufficient holding force to securely clamp a dental tool.

Since dental tools nowadays always have a cylindrical shank according to prescribed standards, it is not possible to use a positive-fit to clamp the shank of the dental tool so as to safeguard it against axial displacement and against turning. Instead, it is necessary to keep the dental tool in position using a force-fit and the resulting frictional forces. Here, the clamping device must be designed such that even under centrifugal forces acting at very high rotational speeds of several 100,000 rpm, it securely holds the dental tool.

Dental handpieces operated using air turbines have a turbine rotor that is supported in a housing by means of a sliding bearing or a ball bearing. The turbine rotor has turbine blades on its circumference, as well as a clamping device for clamping the shank of a dental tool within a housing on whose outside surface the turbine blades are mounted. The current standard for exchanging drilling and grinding tools in dental angled handpieces and dental turbines comprises push-button clamping systems. In such a system, no extra tool is needed to change drills. The advantage here is a clamping system that can be quickly and easily operated, but which nonetheless has sufficient holding force to securely clamp the drill.

In the past, improvements on push-button clamping systems have been repeatedly proposed. For example, DE 102010037791 A1 shows an improvement on clamping systems by exploiting centrifugal force. Here, the centrifugal force, which in the prior art counteracts the clamping effect on the tool, is used to reinforce the clamping effect by a change to the collet and modified installation.

Due to the very high rotational speeds of 200,000-500,000 rpm, exact concentricity of the rotating parts and uniform distribution of mass are extremely important for dental angled handpieces and in particular for dental turbines. Vibrations due to imbalances in the system result in loud, unpleasant noise emissions and considerably reduce the useful life of the bearings as well. In general, a sufficiently uniform distribution of mass in the motors of dental angled handpieces and dental turbines can be achieved by current balancing technology. Here, special attention needs to be paid to the exchangeable tool. By exchanging the tool using the push-button clamping system, the distribution of mass in the rotor can change, which may result in a reduction, but also in an increase, in the residual imbalance remaining after balancing.

The exchangeable tool projects significantly beyond the clamping system in its length, and after clamping can adopt a position at an angle to the rotational axis of the rotor. When clamped at an angle to the rotational axis, the tool wobbles in operation. This induces an unbalance torque that cannot be taken into account in advance by current balancing technology.

SUMMARY OF THE INVENTION

The object of the invention is to provide a clamping device for a dental tool for dental turbine handpieces that allows a more accurate relative position and improved concentricity of the dental tool after clamping.

The clamping device for clamping a dental tool in a dental turbine handpiece comprises a housing in which a collet is disposed that has at least one clamping lever that can be elastically deflected and that extends along the axis A of the tool shank to be clamped. The clamping lever is designed and disposed such that the tool shank can be clamped using the clamping lever. An axially displaceable push-button mechanism having a pressing piece that acts in an axial direction on the clamping levers of the collet is provided in the housing. The tool shank to be clamped is guided and aligned with the aid of first and second guide surfaces in the housing spaced apart from each other along the axis, the guide surfaces being fixedly disposed with respect to the housing, and the second guide surface being formed by an inner circumferential surface of a supporting ring that is fixedly connected to the housing.

The invention provides for the supporting ring to be fixed in an opening in the housing and simultaneously disposed in an opening in the pressing piece, the opening in the pressing piece being larger in size in the direction of the axis A than the axial effective length of the supporting ring, so that the pressing piece can be moved axially with respect to the supporting ring.

It is very important for the guide surfaces that the bore be accurately machined under tight tolerances for insertion of the tool shank, so as to ensure a precise clearance fit having the least possible radial play between the tool shank and the guide surface.

To date it has been known to dispose a guide surface in an appropriate guide bushing that can move axially in the housing. The guide bushing formed a part of the operating mechanism for clamping the tool shank and was thus disposed in the housing so as to be axially moveable. In this guide bushing, the tool shank was then guided with respect to the housing over two clearance fits, which, depending on the component tolerances, resulted in a relatively large radial play, so that in the worst situation, the tool would be very poorly centered and the rotating part of the clamping device together with the tool would thus show severe imbalance.

To improve this situation, the invention provides for both the guide surfaces to be fixedly disposed on the housing, so that only one clearance fit between the tool shank and guide surface is needed. Both guide surfaces feature closed guide surfaces, so that the tool shank is supported and guided over the entire circumferential surface. In this way, the tool shank is much more accurately and precisely aligned in the clamping device.

In particular, the invention provides a supporting ring that is fixedly disposed between the operating device and the collet on or in the housing.

In a first preferred embodiment of the invention, the collet is fixed in the housing and itself forms a first guide surface for the tool shank.

In this embodiment of the invention, the first guide surface is formed by an inner circumferential surface of a sleeve-shaped section of the collet.

The second guide surface is preferably formed by an inner circumferential surface of the supporting ring adjoining the collet that is fixedly connected to the housing.

The tool shank to be clamped is thus guided through the two guide surfaces spaced axially apart from one other that are formed by the sleeve-shaped section of the collet and the supporting ring and that are precisely aligned with respect to the housing.

For clamping the tool shank, the collet preferably comprises two or more clamping levers located opposite each other. At an inner circumference of the clamping levers, clamping surfaces are disposed by means of which the tool shank can be fitted and clamped.

Clamping and releasing the tool shank in the clamping device is effected using a push-button mechanism having a pressing piece that acts axially on the clamping levers of the collet and allows the clamping levers to be released and locked.

In particular, the pressing piece has spreading elements that, on an axial movement of the pressing piece, come to lie against the clamping levers and exert a force acting in a circumferential direction (i.e. a force acting in a radial direction) on the clamping levers. In particular, the spreading elements are pushed in an axial direction between adjacent clamping levers and press them radially apart, whereby clamping surfaces disposed on the clamping levers release the clamped tool shank or respectively allow the tool shank to be inserted.

On retraction of the spreading elements, using a spring load for example, the clamping levers return to their original radial position, whereby the clamping surfaces grip the tool shank and clamp it.

In another embodiment of the invention, a guide surface is not disposed on the collet, but rather the collet is supported in the housing such that it can move in an axial direction.

In this embodiment of the invention, the first guide surface is formed by an inner circumferential surface of a separate guide bushing that adjoins the collet and is fixed in the housing.

The second guide surface is still formed by the supporting ring that is disposed on the other side of the collet and connected to the housing.

In one realization of this preferred embodiment, the spreading elements of the pressing piece can again be inserted axially between adjacent clamping levers of the collet and press them radially apart, whereby clamping surfaces disposed on the clamping levers release the clamped tool shank or respectively allow the tool shank to be inserted.

In another realization of this embodiment, a two-armed clamping lever can be used having first and second lever arms that can be deflected about a virtual fulcrum. The tool shank can be clamped using the first lever arms, the first lever arms having appropriate clamping surfaces. The second, longer lever arms can be spread radially by the spreading elements of the pressing piece, whereby the first, shorter lever arms are accordingly pressed radially inwards about the virtual fulcrum and keep the tool shank clamped. The first and second lever arms are configured such that, on rotation of the clamping device, the second lever arms are additionally deflected radially outwards due to the effect of the centrifugal force, so that the clamping force of the first lever arms is increased.

For all embodiments of the invention, a push-button mechanism is provided for releasing and clamping the tool shank in the clamping device, the push-button mechanism acting in an axial direction on the collet and moving the clamping levers elastically in a radial direction, as required.

In an embodiment of the invention, the respective spreading elements of the pressing piece of the push-button mechanism are pushed axially between the clamping levers and have sloping sliding surfaces that transform the axial movement into a radial movement and press the clamping levers radially outwards, so as to decrease the clamping force of the clamping levers and to release the tool shank.

On releasing the push button, due to the elasticity of the clamping levers, the spreading elements slide out of the clamping levers and the clamping levers exert the required clamping force on the tool shank.

In a further advantageous embodiment, when the push-button mechanism is in a neutral position, a clamping force is still exerted on the clamping levers by means of the spreading elements and the tool shank is clamped between the clamping levers.

When the push-button mechanism is operated, the spreading elements reduce their force on the clamping levers, so that they move back elastically to their normal position and decrease the clamping force on the tool shank, allowing the tool to be exchanged.

Further characteristics and advantages of the invention can be derived from the preferred embodiments of the invention described in the drawings below.

DESCRIPTION OF PREFERRED
EMBODIMENTS OF THE INVENTION

Figure 1:
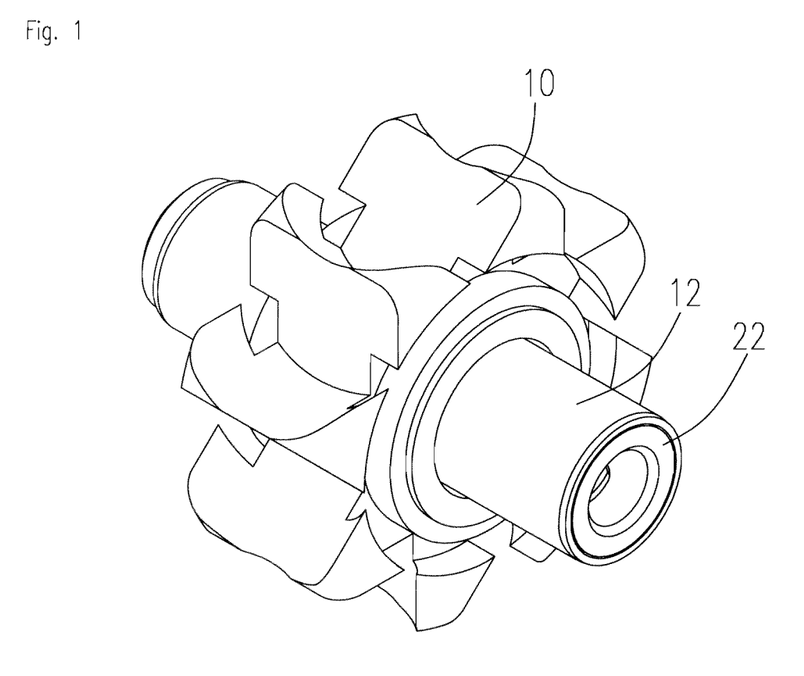
FIG. 1 a perspective view of a dental turbine according to the invention.

FIG. 1 shows a perspective view of a dental turbine that contains a clamping device for a dental tool according to the invention. The dental turbine comprises an impeller 10 having turbine blades that is seated on a housing 12 which encloses the clamping device. The housing 12 is preferably cylindrical or substantially cylindrical and fits into the inside diameter of the impeller 10. The housing 12 may be rotatably supported by means of ball bearings in a dental turbine handpiece (not illustrated). The clamping device and the housing 12 rotate together with the turbine impeller 10. Dental turbines are operated at very high rotational speeds, in the range of 200,000 to 500,000 rpm, for example. This means that during rotation of the dental turbine, a considerable centrifugal force acts on the clamping device.

Figure 2:
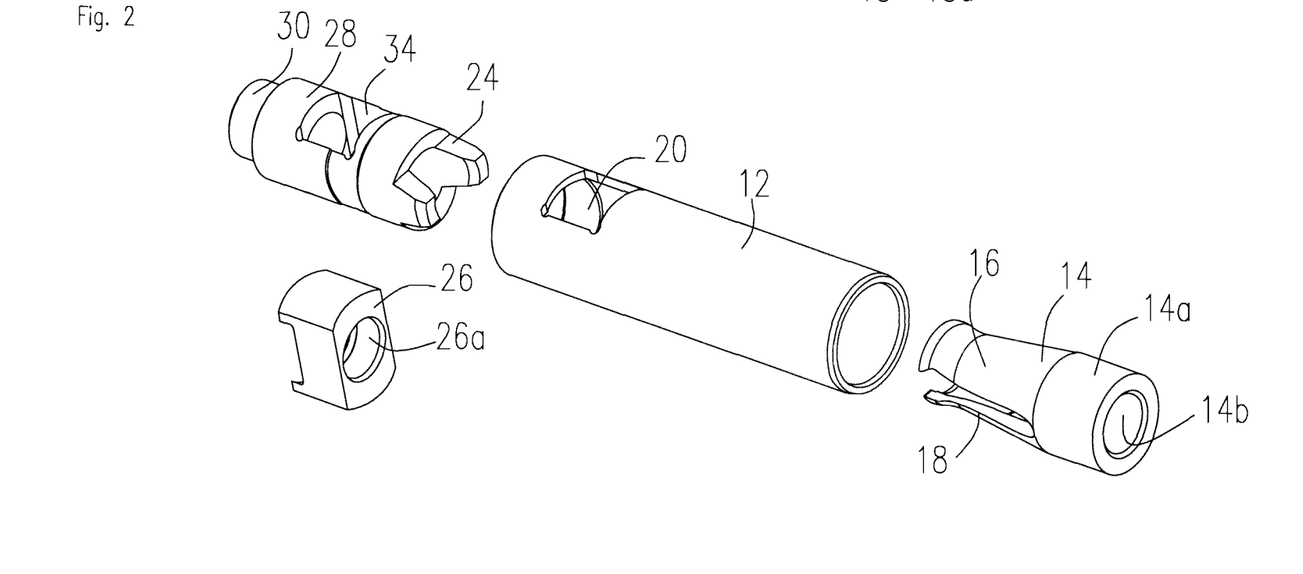
FIG. 2 shows an exploded view of a clamping device according to a first embodiment.
Figure 3:
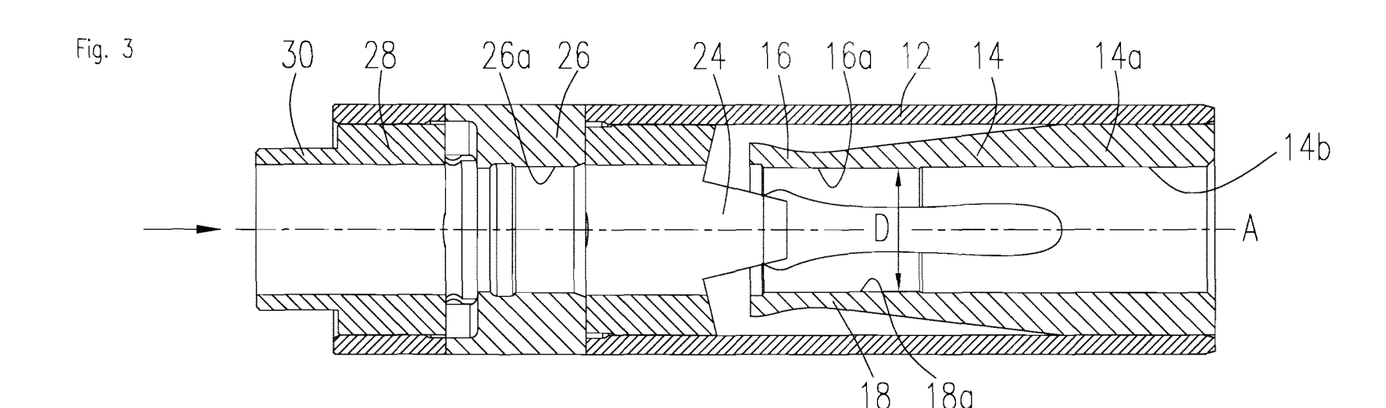
FIG. 3 shows a section of the clamping device of FIG. 2 in a clamped state.

FIGS. 2 and 3 show a first embodiment of the clamping device according to the invention. The clamping device comprises a collet 14 that is fixedly disposed in the housing 12. A pressing piece 28 that is disposed axially moveable in the housing 12 acts on the collet 14 by operating a press button 30. The press button 30 may preferably be integrally formed with the pressing piece 28 as one piece. According to the invention, a supporting ring 26 is disposed in an opening 34 in the pressing piece 28 and fixed in an opening 20 in the housing 12.

The collet 14 has a sleeve-shaped section 14*a* that is fixed to an inner circumference of the housing 12. First and second clamping levers 16, 18 are disposed opposite each other on the sleeve-shaped section 14*a* and are directed in an axial direction towards the interior of the housing 12. The clamping levers 16, 18 can be elastically deformed and radially deflected. The clamping levers 16, 18 extend substantially parallel to the axis A of the tool shank to be clamped. The collet 14 is preferably made of metal, such as stainless steel. The lever arms of the clamping levers 16, 18 have clamping surfaces 16*a*, 18*a* on their inner circumference that are used for gripping or clamping the tool shank.

The sleeve-shaped section 14*a* of the collet 14 and the supporting ring 26 are spaced as far apart from one another as possible and form guide surfaces for guiding and centering the tool shank to be clamped.

The collet 14 is disposed and fixed at one end of the housing 12. The tool shank of the tool to be clamped is inserted from the direction of the sleeve-shaped section 14*a* of the collet 14.

Adjoining the free clamping levers 16, 18 of the collet 14 is a pressing piece 28 having a press button 30 protruding from the housing 12 and disposed axially moveable in the housing, where respective spreading elements 24 at the end of the pressing piece 28 can be made to abut the clamping levers 16, 18 of the collet 14.

The pressing piece 28 has an opening 34 in which the supporting ring 26 is disposed. The opening 34 is larger in size in an axial direction (in the direction of the axis A) than the axially effective length of the supporting ring 26, so that the pressing piece 28 can be moved axially with respect to the supporting ring 26, whereas the supporting ring 26 is fixedly connected to the housing.

For installing the supporting ring 26, the housing 12 also preferably has an opening 20 into which the supporting ring 26 can be inserted and fixedly connected to the housing, by welding for example.

The supporting ring 26 is thus fixed with respect to the housing 12, whereas the pressing piece 28 can move axially in the direction of the axis A with respect to the housing and the supporting ring 26.

FIG. 3 shows the clamping device in a clamped state, i.e. respective clamping surfaces 16*a* and 18*a* that are disposed on the inner circumference of the clamping levers 16, 18 define a clamping diameter D which, in a clamped state, rests against the outside diameter of the tool shank, so that the tool shank is clamped in the region of the clamping surfaces 16*a*, 18*a*.

By operating the press button 30, the pressing piece 28 can move axially in the direction of the arrow towards the collet 14. The sloped or tapered spreading elements 24 of the pressing piece 28 thereby enter the space between the two clamping levers 16, 18 of the collet 14. Due to the respectively sloped surfaces of the spreading elements 24, the axial movement of the spreading elements 24 is transformed into a radial movement of the two clamping levers 16, 18.

This means that the clamping diameter D increases through spreading the two clamping levers 16, 18 and the clamping surfaces 16*a* and 16*b* disengage from the tool shank or respectively allow a tool shank to be inserted in the clamping device due to the larger clamping diameter D.

The tool shank is inserted from the right, i.e. from the side of the sleeve-shaped section 14*a* of the collet 14, into the device, passing through the collet 14 and right into the bore of the supporting ring 26, where the supporting ring may have an end stop that determines the final position of the tool shank.

The tool shank is guided through the first guide surface 14*b* on the sleeve-shaped section 14*a* as well as the second guide surface 26*a* of the supporting ring 26 and centered with respect to the rotational axis A.

Since the collet 14, i.e. its sleeve-shaped section 14*a* as well, and the supporting ring 26 are fixed and aligned accordingly on or in the housing 12, the tool shank is guided and centered within the range of manufacturing tolerances of the contact surfaces 14*b* and 26*a* in the tool.

If the operating button 30 is released, due to the radial preload of the clamping levers 16, 18 and their sloped surfaces, the spreading elements 24 slide in the opposite direction to the arrow, out of the space between the two clamping levers 16, 18 and, due to their elasticity, the clamping levers move radially inwards in the direction of the axis A back to their original position. The clamping diameter D thereby decreases and the clamping surfaces 16*a* and 18*a* abut against the outside circumference of the tool shank and clamp it firmly in the collet 14.

The supporting ring 26 is flattened at two opposing sides so that there remains enough space between the housing 12 and the supporting ring 26 for the relevant parts of the pressing piece 28, i.e. the pressing piece remains axially moveable about the supporting ring.

Figure 4:
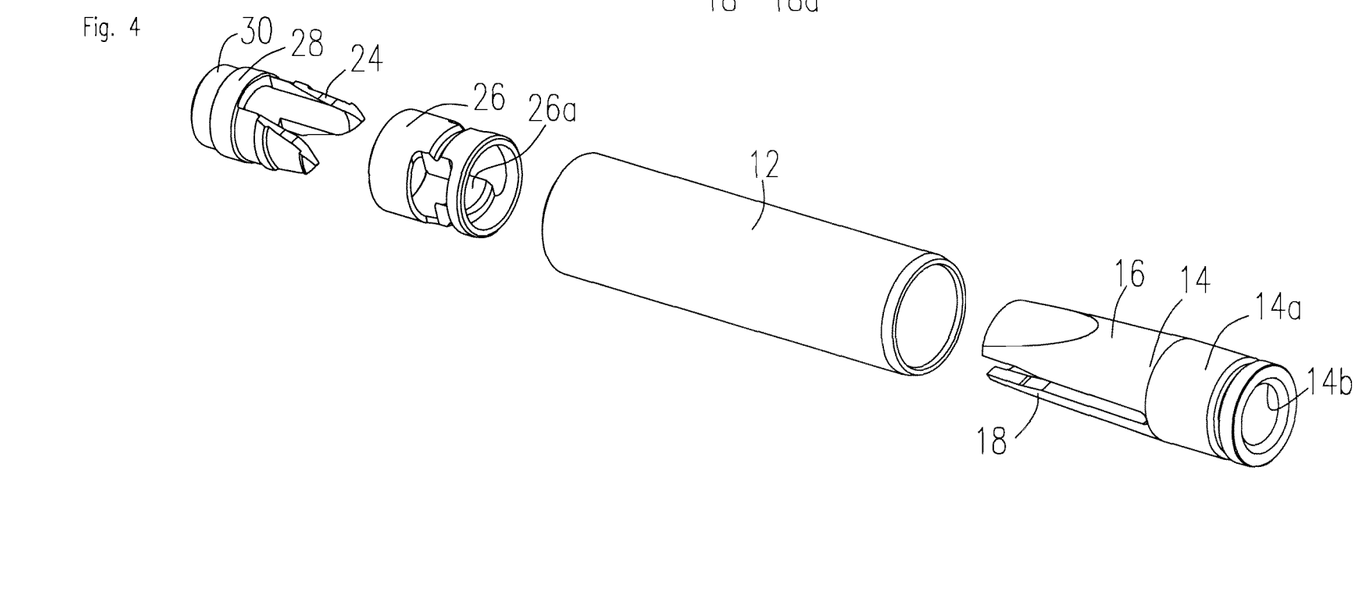
FIG. 4 shows an exploded view of a clamping device according to a second embodiment.
Figure 5:
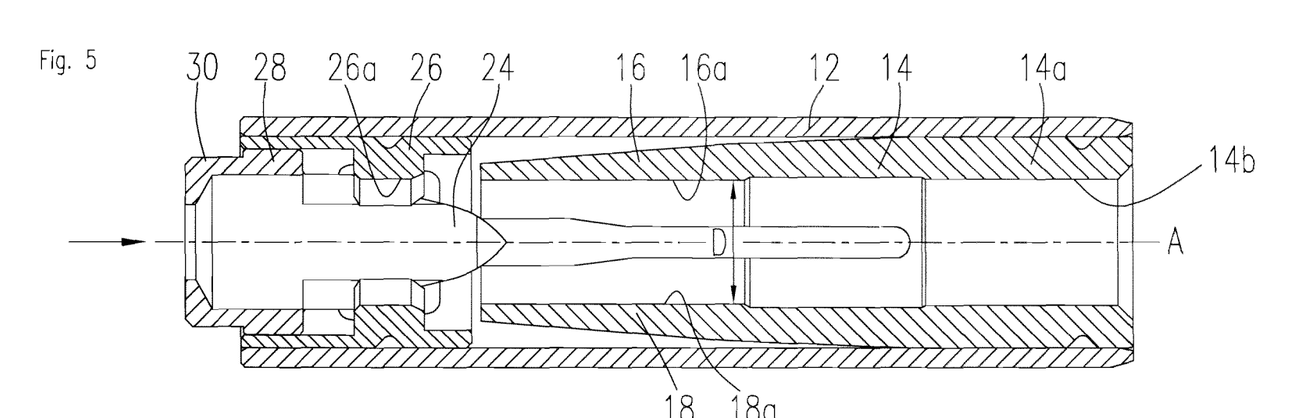
FIG. 5 shows a section of the clamping device of FIG. 4 in a clamped state.

FIGS. 4 and 5 show a further embodiment of a tool clamping system that corresponds substantially with the first embodiment according to FIGS. 2 and 3 in its functionality.

For the embodiments in FIGS. 4 and 5 the same reference numbers are used for the same components. Reference is made to the above description of the individual components.

The second embodiment according to FIGS. 4 and 5 differs from the first embodiment through the shape of the individual components, in particular the shape of the collet 14, the supporting ring 26 and the pressing piece 28.

The collet 14 again defines a sleeve-shaped section 14*a* that forms the first guide surface 14*b* for the tool shank.

Also in evidence are the two clamping levers 16, 18 that are directed in the direction of the pressing piece 28 parallel to the axis A, and between which a free space is formed.

The legs of the clamping levers 16, 18 form the clamping diameter D that is defined by respective clamping surfaces 16*a*, 18*a*.

The supporting ring 26 is fixedly disposed in the housing, has a sleeve-like shape, and forms two defined guide surfaces 26*a* that are disposed opposite each other on the inner circumference of the supporting ring.

The pressing piece 28 is moveably disposed in the supporting ring 26, respective spreading elements 24 being guided through the supporting ring 26 and coming to lie in the space between the two clamping levers 16, 18. The spreading elements 24 are again given sloped spreading surfaces. At the end of the pressing piece, a press button 30 is disposed.

The functionality is again the same as described in FIGS. 2 and 3. By pressing the press button 30 in the direction of the arrow, the spreading elements 24 insert themselves between the two lever arms 16, 18, whereby the clamping diameter D increases and the clamped tool shank is released or respectively can be inserted.

Once the press button 30 has been released, the two clamping levers 16, 18 return radially inwards to their starting position, whereby the clamping surfaces 24 are pushed in the opposite direction to the arrow and the pressing piece 28 returns to its starting position.

Figure 6:
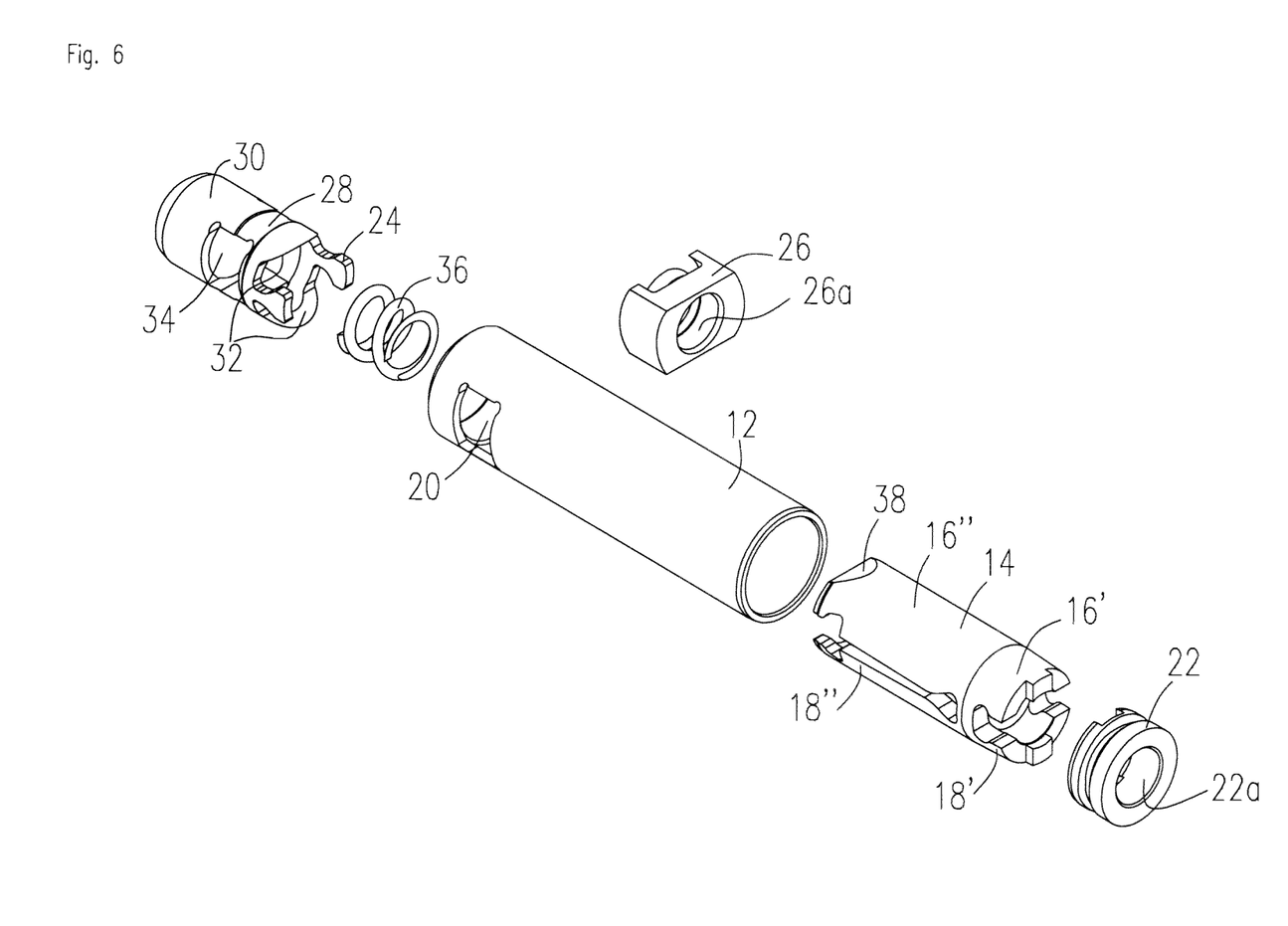
FIG. 6 shows an exploded view of a clamping device according to a third embodiment.
Figure 7:
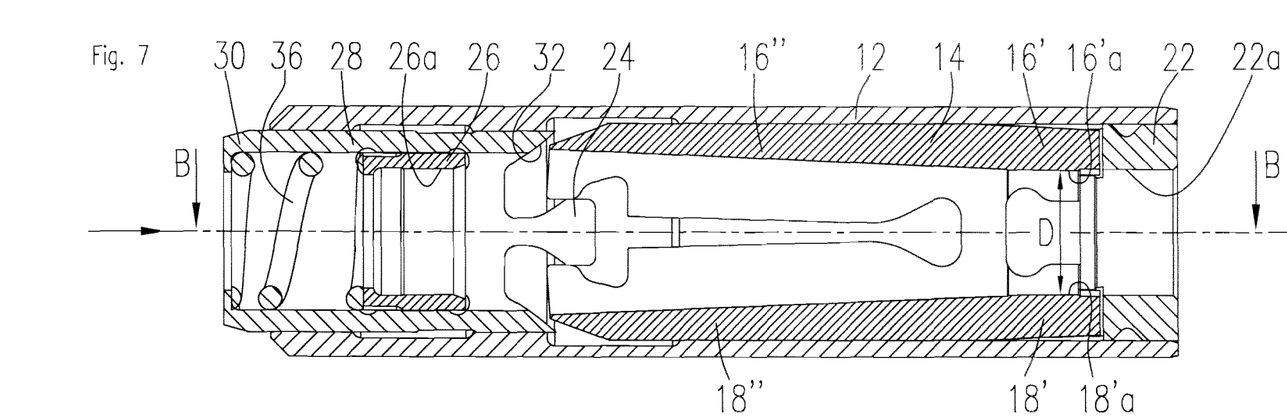
FIG. 7 shows a section of the clamping device of FIG. 6 in a clamped state.
Figure 8:
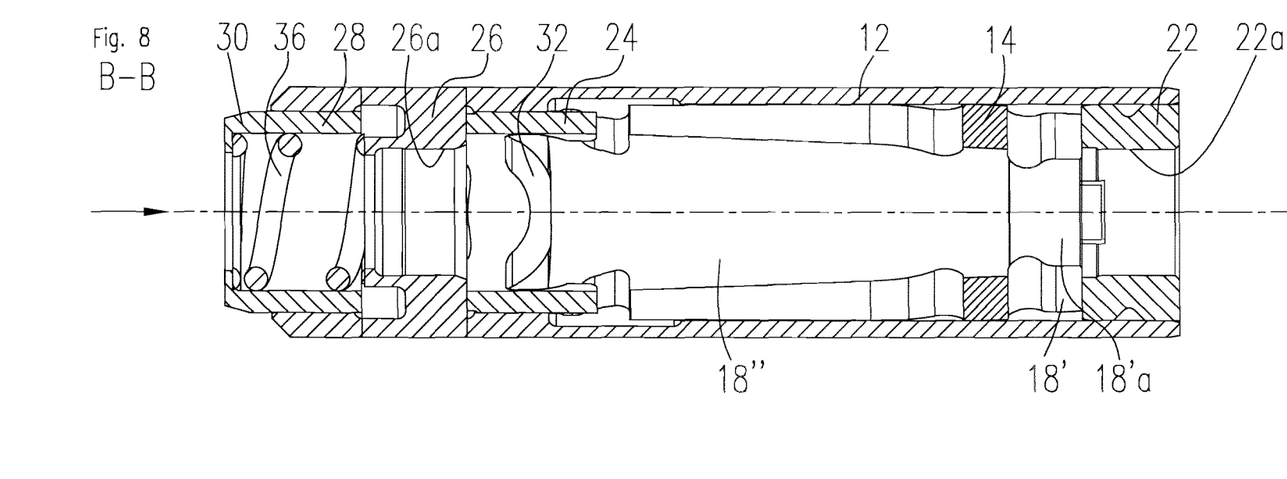
FIG. 8 shows a section of the clamping device along the line B-B of FIG. 7.

Finally, in FIGS. 6 to 8 a further embodiment of the invention is illustrated.

Insofar as this third embodiment corresponds to the first two embodiments, the same reference numbers are used. Reference is made to the above description of the individual components and their functionality.

The main difference to the embodiments of the previous examples is that the collet 14 is not firmly fixed in the housing 12, but rather disposed in the housing so as to allow a slight axial movement.

Moreover, in contrast to the first two embodiments of the invention, the collet 14 does not function as a guide for the tool shank, i.e. the collet 14 does not have any guide surfaces for the tool shank.

Moreover, this embodiment differs from the previous embodiments through the design and arrangement of the collet 14.

The collet 14 comprises two clamping levers 16, 18 having longer lever arms 16" and 18" located opposite one another as well as two shorter lever arms 16' and 18' located opposite one another and extending in the other direction.

The two longer lever arms 16" and 18" of the collet 14 are directed in the direction of the pressing piece 28, whereas the shorter lever arms 16', 18' are directed in the direction of a guide bushing 22 that has a corresponding first guide surface 22a for guiding the tool shank. The guide bushing 22 is disposed on the side of the clamping device on which the tool shank is introduced.

The collet 14 is bordered in the housing 12 by the guide bushing 22 and by the pressing piece 28 and operated by the pressing piece.

The collet 14 has projections directed in the direction of the guide bushing 22 that engage in respective depressions in the guide bushing 22 and thus act as a safeguard against turning for the collet 14, since the guide bushing 22 is fixedly disposed in the housing.

Spreading elements 24 are provided on the pressing piece 28 that engage between the two longer lever arms 16", 18", namely in respective dove-tail shaped grooves having sloped sliding surfaces. The spreading elements 24 are also dove-tailed in shape having respective sloped sliding surfaces.

The collet 14 is operated using a press button 30 that forms a part of the pressing piece 28 and a pressure spring 36 disposed between the pressing piece 28 and the stationary supporting ring 26.

The pressure spring 36 forms a return mechanism that is described below.

FIGS. 7 and 8 show the clamping device in a clamped state, i.e. when the press button 30 is not being operated.

Through the pressure spring 36, the pressing piece 28 is pressed away from the supporting ring 26 in the opposite direction to the arrow, the dove-tail shaped spreading elements 24 being pulled out of the dove-tail shaped recesses between the two longer lever arms 16" and 18" of the collet 14.

Due to the sloped surfaces of the spreading elements 24 inclined in the direction of the pressing piece 28 and the corresponding sloped counter surfaces in the recesses in the lever arms 16", 18", the longer lever arms 16" and 18" are spread apart radially outwards by the spreading elements. This elastic pressure on the longer lever arms 16", 18" is passed on to the shorter lever arms 16' and 18' which are now pressed contrary to this acting force radially inwards in the direction of the axis A, so that the clamping diameter D decreases. In this way, the clamping surfaces 16'a, 18'a disposed on the shorter lever arms 16' and 18' abut the tool shank and clamp it. This represents the clamped state.

By operating the press button 30, the pressing piece 28 is pushed in the direction of the arrow towards the collet 14, the supporting ring 26 remaining stationary and forming a stopper for the press button of the pressing piece 28. During this pressing movement, the spreading elements 24 move into the dove-tail shaped cavity between the longer lever arms 16" and 18", whereby the radial pressure on the longer lever arms 16", 18" is removed and the longer lever arms 16" and 18" can move elastically radially inwards into their relaxed state.

The shorter lever arms 16', 18' thereby move about a virtual fulcrum radially outwards, the clamping diameter D increasing and the clamping surfaces 16'a and 18'a lifting away from the tool shank and releasing it. It can be provided that in the non-preloaded state, the clamping diameter D of the collet is smaller than the diameter of the tool shank and the collet is opened by means of wedge-shaped inside surfaces 32 of the pressing piece 28. For this purpose, the pressing piece 28 has wedge-shaped inside surfaces 32 and when, on operation of the pressing piece, the wedge-shaped inside surfaces 32 slide along the slopes 38 of the longer lever arms 16", 18" of the clamping levers 16, 18, then the longer lever arms 16", 18" are pressed in the direction of the axis of the tool shank to be clamped and the clamping diameter D at the shorter lever arms 16', 18' is opened.

Once the tool has been removed or exchanged, pressure can be removed from the press button 30, whereby the pressing piece 28 moves again to its far left position through the force of the spring 36. The sliding surfaces of the spreading elements 24 thereby again slide along the sliding surfaces of the longer lever arms 16" and 18" of the collet 14 and spread them, so that clamping, as described above, is once more activated.

In the embodiment of the invention according to FIGS. 4 and 5, the supporting ring 26 with its guide surfaces is not closed. Here, there are two guide surfaces located opposite one another. The supporting ring may be mounted in an axial direction in the housing.

In the two solutions according to FIGS. 2 and 3 as well as FIGS. 6-8, a closed supporting ring having a closed guide surface is used that is mounted radially through an opening in the housing 12 of the clamping system.

According to an advantageous embodiment of the invention, the second guide surface in the supporting ring can be given a slight taper, whereby the tool is centered when the tool shank is inserted into the tapered guide bore.

The last-mentioned embodiment of FIGS. 6-8 is a clamping system supported by the centrifugal force, i.e. on rotation of the housing and the collet, the longer lever arms 16" and 18" of the collet can spread further from the axis A of the tool shank to be clamped through the centrifugal force acting on the lever arms 16", 18". Through such spreading supported by the centrifugal force, the clamping force that acts on the shorter lever arms 16' and 18' is increased as the rotational speed of the clamping system increases.

IDENTIFICATION REFERENCE LIST

10 Impeller
12 Housing

14 Collet
14a Sleeve-shaped section
14b Guide surface
16 Clamping lever
16a Clamping surface
18 Clamping lever
18a Clamping surface
16', 18' First, short lever arm
16'a, 18'a Clamping surface
16", 18" Second, longer lever arm
20 Opening
22 Guide bushing
22a Guide surface
24 Spreading element
26 Supporting ring
26a Guide surface
28 Pressing piece
30 Press button
32 Inside surface
34 Opening
36 Pressure spring
38 Slope
A Axis of the tool shank to be clamped
D Clamping diameter

The invention claimed is:

1. A clamping device for clamping a dental tool in a dental turbine handpiece comprising:
    a housing in which a collet is disposed, the collet having at least two clamping levers that can be elastically deflected and extend along the axis (A) of a tool shank to be clamped, the clamping levers are designed and arranged for clamping the tool shank,
    a push-button mechanism moveably disposed in the housing and provided with a pressing piece that acts in an axial direction on the clamping levers of the collet, wherein the tool shank to be clamped is guided and aligned in the housing with the aid of first and second guide surfaces that are spaced apart from one another along the axis (A) and that are fixedly disposed with respect to the housing, wherein the collet defines a sleeve-shaped section that forms the first guide surface for the tool shank,
    a supporting ring fixedly disposed in the housing, having a sleeve-like shape, and forming second guide surfaces that are disposed opposite each other on the inner circumference of the supporting ring,
    the push-button mechanism comprising a press button and the pressing piece having spreading elements with sloped spreading surfaces that act in an axial direction on the clamping levers of the collet,
    wherein the pressing piece of the push-button mechanism is moveably disposed in the supporting ring, and wherein the spreading elements are guided through the supporting ring and come to lie in the space between the clamping levers.

2. A clamping device according to claim 1, wherein the collet has two or more clamping levers located opposite one another.

3. A clamping device according to claim 1, wherein the sloped spreading surfaces of the spreading elements upon an axial movement of the pressing piece come to lie against the clamping levers and exert a force acting in a radial direction on the clamping levers.

4. A clamping device according to claim 1, wherein the collet is fixed in the housing.

5. A clamping device according to claim 1, wherein the spreading elements come to lie between adjacent clamping levers and press them radially apart, whereby clamping surfaces disposed on the clamping levers release the clamped tool shank.

6. A clamping device according to claim 1, wherein once the press button is released, due to the radial preload of the clamping levers and their sloped surfaces, the spreading elements slide in the direction of the pressing piece out of the space between the two clamping levers and, due to their elasticity, the clamping levers move radially inwards in the direction of the axis (A) back to their original position.

* * * * *